US00PP20041P2

(12) United States Plant Patent
Blake

(10) Patent No.: US PP20,041 P2
(45) Date of Patent: Jun. 2, 2009

(54) ***SILENE* PLANT NAMED 'FIREFLY'**

(50) Latin Name: *Silene diocia*
Varietal Denomination: Firefly

(76) Inventor: Gwendyth Blake, 1A Moorfield Road, Woodbridge, Suffolk IP12 4JN (GB)

( * ) Notice: Subject to any disclaimer, the term of this patent is extended or adjusted under 35 U.S.C. 154(b) by 0 days.

(21) Appl. No.: 12/156,711

(22) Filed: Jun. 3, 2008

(51) Int. Cl.
*A01H 5/00* (2006.01)

(52) U.S. Cl. ..... Plt./481

(58) Field of Classification Search ..... Plt./481
See application file for complete search history.

*Primary Examiner*—Kent L Bell
(74) *Attorney, Agent, or Firm*—C. A. Whealy

(57) ABSTRACT

A new and distinct cultivar of *Silene* plant named 'Firefly', characterized by its upright to outwardly spreading plant habit; freely branching habit; dark green-colored leaves; freely flowering habit; and fully double red purple-colored flowers.

1 Drawing Sheet

Botanical designation: *Silene diocia.*
Cultivar denomination: 'Firefly'.

BACKGROUND OF THE INVENTION

The present invention relates to a new and distinct cultivar of *Silene,* botanically known as *Silene diocia* and hereinafter referred to by the name 'Firefly'.

The new *Silene* is a naturally-occurring whole plant mutation of an unnamed selection of *Silene diocia,* not patented. The new *Silene* was discovered and selected by the Inventor as a single flowering plant from within a population of plants of the selection in a controlled outdoor nursery environment in Woodbridge, Suffolk, United Kingdom in June, 2001.

Asexual reproduction of the new *Silene* by divisions in a controlled outdoor nursery environment in Woodbridge, Suffolk, United Kingdom, since May, 2002, has shown that the unique features of this new *Silene* are stable and reproduced true to type in successive generations.

SUMMARY OF THE INVENTION

Plants of the new *Silene* have not been observed under all possible environmental conditions. The phenotype may vary somewhat with variations in environment such as temperature and light intensity without, however, any variance in genotype.

The following traits have been repeatedly observed and are determined to be the unique characteristics of 'Firefly'. These characteristics in combination distinguish 'Firefly' as a new and distinct cultivar:

1. Upright to outwardly spreading plant habit.
2. Freely branching habit.
3. Dark green-colored leaves.
4. Freely flowering habit.
5. Fully double red purple-colored flowers.

Plants of the new *Silene* differ from plants of the parent selection in the following characteristics:

1. Plants of the new *Silene* have double flowers whereas plants of the parent selection have single flowers.

2. Plants of the new *Silene* have smaller flowers than plants of the parent selection.
3. In Woodbridge, Suffolk, United Kingdom, plants of the new *Silene* flower from May to September whereas plants of the parent selection flower from April until July.
4. Plants of the new *Silene* and the parent selection differ in flower color as plants of the parent selection have pale to dark pink-colored flowers.

Plants of the new *Silene* can be compared to plants of the *Silene* 'Rosea Plena', not patented. In side-by-side comparisons in Bressingham, United Kingdom, plants of the new *Silene* differed from plants of the 'Rosea Plena' in the following characteristics:

1. Plants of the new *Silene* had smaller flowers than plants of 'Rosea Plena'.
2. Plants of the new *Silene* had fully double flowers whereas plants of 'Rosea Plena' had semi-double to double flowers.
3. Plants of the new *Silene* had red purple-colored flowers whereas plants of 'Rosea Plena' had pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Silene.*

The photograph at the bottom of the sheet comprises a side perspective view of a typical flowering plant of 'Firefly' grown in a container.

The photograph at the top of the sheet is a close-up view of typical flowers of 'Firefly'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the winter and early spring in a polyethylene-covered greenhouse in Lancaster, Pa. for four months. During the production of the plants, day temperatures ranged from 18° C. to 27° C. and night temperatures averaged 18° C.

Botanical classification: *Silene diocia* 'Firefly'.

Parentage: Naturally-occurring whole plant mutation of an unnamed selection of *Silene diocia,* not patented.

Propagation:

*Type.*—By divisions.

*Time to initiate roots.*—About 15 days at 21° C. to 25° C.

*Time to produce a rooted young plant.*—About 30 days at 21° C. to 25° C.

*Root description.*—Medium to fine, fibrous; close to 158B in color.

*Rooting habit.*—Freely branching; dense.

Plant description:

*Form.*—Herbaceous perennial. Upright and outwardly spreading plant habit; freely branching habit; vigorous growth habit. Flowers arranged in terminal and axillary clusters.

*Plant height.*—About 58 cm.

*Plant width.*—About 58 cm.

*Lateral branch description.*—Quantity per plant: About six primary branches. Length: About 56 cm. Diameter: About 4 mm. Internode length: About 2.4 cm. Strength: Strong. Texture: Hirsute. Color: Close to 146B.

Foliage description:

*Arrangement.*—Opposite, simple.

*Length.*—About 8.6 cm.

*Width.*—About 5 cm.

*Shape.*—Obovate to elliptical.

*Apex.*—Acute.

*Base.*—Attenuate to truncate.

*Margin.*—Entire.

*Texture, upper and lower surfaces.*—Hirsute.

*Venation pattern.*—Pinnate; arcuate.

*Color.*—Developing foliage, upper surface: Close to 146A. Developing foliage, lower surface: Close to 146B. Fully expanded foliage, upper surface: Close to 147A; venation, 146B. Fully expanded foliage, lower surface: Close to 146B; venation, close to 146B.

*Petiole length.*—About 6.8 cm.

*Petiole diameter.*—About 6 mm.

*Petiole texture, upper and lower surfaces.*—Pubescent.

*Petiole color, upper surface.*—Close to 146D.

*Petiole color, lower surface.*—Close to 147C.

Flower description:

*Flower arrangement and shape.*—Fully double rounded flowers arranged in terminal and axillary clusters; flowers face mostly upright to outwardly. Freely flowering, about 87 flowers and flower buds per lateral branch.

*Natural flowering season.*—Continuous flowering during May in Pa.

*Flower longevity on the plant.*—About five days; flowers persistent.

*Fragrance.*—None detected.

*Flower buds.*—Length: About 1.6 cm. Diameter: About 8 mm. Shape: Ovoid; longitudinally ridged. Color: Close to N74B to N74C.

*Flowers.*—Diameter: About 1.9 cm. Depth (height): About 1.5 cm.

*Petals/petaloids.*—Arrangement: About 32 in about four tight whorls. Length: About 1.1 cm to 1.5 cm. Width: About 4 mm to 7 mm. Shape: Narrowly cordate. Apex: Emarginate. Base: Acute. Margin: Entire. Texture, upper and lower surfaces: Smooth, glabrous; satiny. Color: When opening, upper and lower surfaces: Close to 74B. Fully opened, upper and lower surfaces: Towards the apex, close to 72C; center, close to NN155B; towards the base, close to 160C to 160D.

Sepals: Arrangement: About six to seven in a single whorl; fused into a bowl-shape calyx. Length: About 9 mm. Width: About 7 mm. Apex: Acute. Margin: Entire. Texture, upper surface: Smooth, glabrous. Texture, lower surface: Pubescent. Color, upper surface: Close to 146C. Color, lower surface: Close to 147B tinted with close to 176C.

*Peduncles.*—Length: About 7 mm. Diameter: About 1.5 mm. Aspect: About 45° to 55° from vertical. Strength: Strong. Texture: Pubescent. Color: Close to 146B.

*Reproductive organs.*—Reproductive structures are transformed into petaloids.

*Seed/fruit.*—Seed and fruit production has not been observed.

Disease/pest resistance: Plants of the new *Silene* have not been noted to be resistant to pathogens and pests common to *Silene.*

Garden performance: Plants of the new *Silene* have exhibited good tolerance to rain, wind and temperatures ranging from about −3° C. to about 30° C.

It is claimed:

1. A new and distinct *Silene* plant named 'Firefly' as illustrated and described.

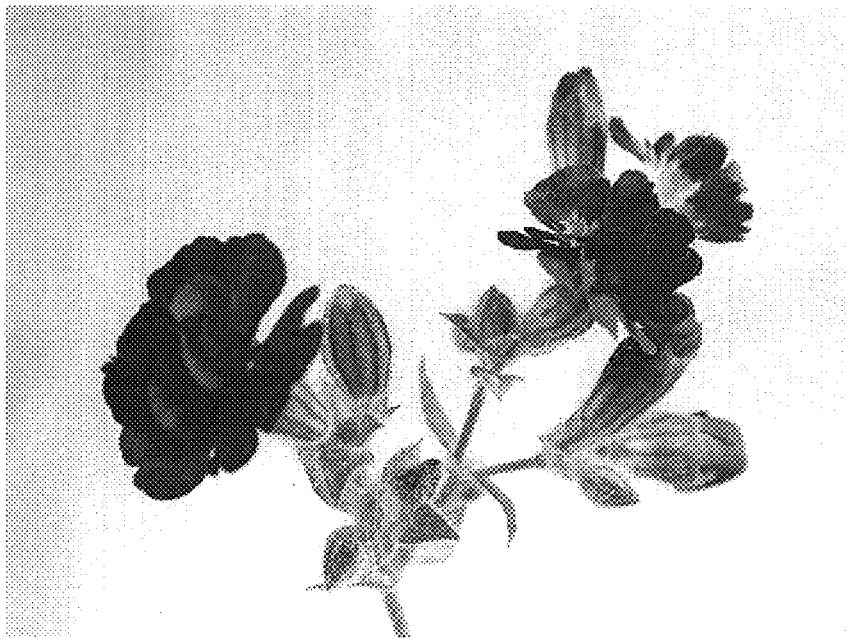
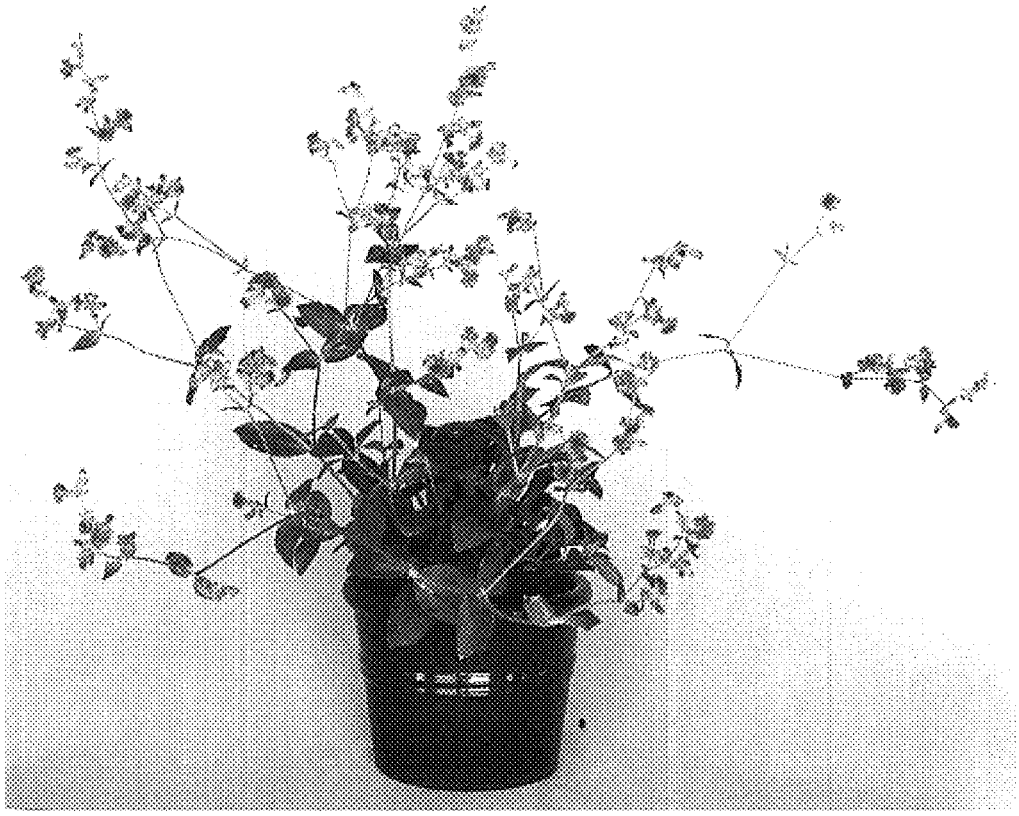

* * * * *